US006328759B1

(12) United States Patent
Zhang

(10) Patent No.: US 6,328,759 B1
(45) Date of Patent: Dec. 11, 2001

(54) SPINAL THREE-DIMENSIONAL ORTHOPEDIC EQUIPMENT

(76) Inventor: Ji Ling Zhang, Dianli Hospital, No. 117, Jingshi Road, Jinan City, Shandong Province (CN), 250001

( * ) Notice: Subject to any disclaimer, the term of this patent is extended or adjusted under 35 U.S.C. 154(b) by 0 days.

(21) Appl. No.: 09/403,902

(22) PCT Filed: Apr. 29, 1997

(86) PCT No.: PCT/CN97/00038

§ 371 Date: Oct. 28, 1999

§ 102(e) Date: Oct. 28, 1999

(87) PCT Pub. No.: WO98/48743

PCT Pub. Date: Nov. 5, 1998

(51) Int. Cl.[7] ........................................ A61F 5/00

(52) U.S. Cl. ........................ 606/242; 606/241; 606/240; 5/613; 5/616

(58) Field of Search ........................ 606/237, 240–245; 602/32, 33, 35; 5/618, 612–613, 616

(56) References Cited

U.S. PATENT DOCUMENTS 1,205,649 * 11/1916 Miller .
1,269,354 * 6/1918 Williams .
1,286,166 * 11/1918 Williams .
1,453,013 * 4/1923 Koenigkramer .
1,602,196 * 10/1926 Iverson .
3,771,518 * 11/1973 Greissing ........................ 128/71
4,144,880 * 3/1979 Daniels ........................ 128/71
4,722,328 * 2/1988 Scott ........................ 128/74
5,050,589 * 9/1991 Engle ........................ 128/25
5,192,306 * 3/1993 Scott et al. ........................ 606/243
5,645,079 * 7/1997 Zahiri et al. ........................ 128/846
5,794,286 * 9/1998 Scott et al. ........................ 5/611

* cited by examiner

*Primary Examiner*—Justine R. Yu
(74) *Attorney, Agent, or Firm*—Gary M. Nath; Harold L. Novick; Marvin C. Berkowitz

(57) ABSTRACT

The object of the present invention is to provide a three-dimensional spine remedying apparatus, which offers more comprehensive functions and better curative effects, and frees the patient from discomfort during the process of treatment. The apparatus of the invention includes: a frame; a cephalothoracic board and a driving device thereof; a hip-leg board and a driving device thereof; a low-speed draught device; a hip board capable of rotating around the axle Z and a driving device thereof; a device for securing the body of the patient and an adjusting means thereof. The driving devices of said cephalothoracic board, hip-leg board and hip board are high-speed driving devices employing electromagnetic force. Said hip-leg board and hip board are capable of not only rotating by a predetermined angle, but also making high-speed angular oscillation. In addition, in said driving device of said cephalothoracic board, a clutch is provided for linking up the high-speed movement of the magnetic driving device of the cephalothoracic board with the low-speed movement of the said draught device.

8 Claims, 10 Drawing Sheets

A-A

B-B

C-C

SPINAL THREE-DIMENSIONAL ORTHOPEDIC EQUIPMENT

FIELD OF THE INVENTION

The present invention relates to medical appliances for treating parenchyma trauma between vertebras and, in particular, to a therapeutic apparatus for remedying three-dimensional displacements between vertebras.

BACKGROUND OF THE INVENTION

Diseases with parenchyma trauma between vertebras, such as prolapse of lumbar intervertebral disc, cervical spondylopathy and thoraxlumbar rear joint disorder, are familiar diseases which bring tremendous suffering to the patient. Medication is not efficacious to these diseases. In addition, the cost of operation is high, while the patient has to endure the long operation and tremendous suffering thereafter. Therefore, the applicable scope of operation is limited.

Remedying apparatus for treating these diseases have been widely used. For example, many types of traction apparatus have been developed. However, all the existing traction apparatus adopts linear traction, only in one direction. Since it not can remedy the angular displacement between the vertebras, the curative effect is not ideal. Further, the process of draught is usually performed by manual labor, or by hydraulic or mechanical transmission, and the draught velocity is low, and the patient may feel uncomfortable in the process of draught, which has an adverse effect on the treatment. In addition, trauma would be caused when the distance of draught exceeds the limit because of misoperation.

The inventor of the invention has found that, for prolapse of lumbar intervertebral disc and cervical spondylopathy, the displacements between the affected vertebras usually occur in three dimensions. That is, linear displacements and angular displacements may occur along the longitudinal axle, lateral axle and vertical axle between the upper vertebra and the lower vertebra, so that the stress between the vertebras is changed to break the stable and coordinate state. Therefore, not only the fibre rings are broken and the nucleus pulposus protrudes due to the unevenly distributed forces, but also the rear joint, and the muscles and ligaments attached thereto or the nerves and blood vessels nearby are affected. This makes the patient suffer from pain in the neck, shoulders, waist and legs. As time passes, to compensate for the above situation, hyperosteogeny and ligament pachismus will appear at the positions to bear larger force with more serious consequence. The inventor has thus come to see that it is necessary to remedy the lineal displacements and the angular displacements between the vertebras in three dimensions rather than to correct the lineal displacements in one direction alone. Only in this case is it possible to remedy the misalignment among small joints between the vertebras, and to eliminate the abnormal draught, squeeze or stimulation on the muscles, the ligaments, the nerves and the blood vessels nearby, so that the structure between the vertebras can be restored from a state of bearing uneven forces to a natural and coordinate state.

Based on the pathology described above and the rich experience in bone setting accumulated over the years, the present inventor has filed an application titled "Angulate Rotating Multifunctional Draught Bed", which has been granted a Chinese patent (CN206 464 3U) and a Japanese Patent (Patent number: 95-79823). Said draught bed comprises: a frame, a cephalothoracic board, a hip-leg board, a draught device, a device for the horizontal rotating of said boards, a device for the vertical rotating of said boards and a control device. Said cephalothoracic board is driven by said draught device to move horizontally along the longitudinal axle of said draught bed. Said hip-leg board can swing around the lateral axle (Y) of said bed to form a certain angle with the vertebra's longitudinal axle. Furthermore, said hip-leg board is able to rotate to the left or the right around the longitudinal axle (X) of said bed to twist the vertebras. It is verified by clinical applications that the curative effect of said draught bed for treating prolapse of lumbar intervertebral disc is fairly good.

Although the hip-leg board of the said patented draught bed is capable of rotating around the longitudinal axle (X) and the lateral axle (Y), it still cannot rotate around the vertical axle (Z). Accordingly, the vertebra twisting in that direction has to be corrected manually. Furthermore, because the movement mechanism is hydraulically driven or mechanically driven, the speed is relative low. This makes the patient uneasy when being treated. In addition, the noise of the hydraulic driving is loud and not suitable for medical to the environment of medical treatment . Also, because the high-speed traction and the low-speed traction of the patented bed are transmitted separately, and the bed is not convenient to medical treatment. In addition, said hip-leg board can rotate to only one side each time when said draught bed is rotating around the longitudinal axle, and it takes a lot of time for the board to rotate to the other side. Said draught bed not can move between the two sides quickly and repeatedly. Hence, there is no function provided for releasing the tension of the muscles surrounding the vertebras, and it is adverse to the treatment of the strain of lumbar muscles and the alignment of the vertebras.

OBJECTS OF THE INVENTION

The object of the present invention is to further improve the Chinese Patent CN2064643U "Multi-functional Draught Bed", and to provide a three-dimensional spine remedying apparatus, which has a better curative effect and more convenient operation and makes the patient feel safe and comfortable during the treatment.

Said Chinese Patent CN2064643U is the most relative document of the present invention, which is entirely based on the disclosure of the foregoing patent.

SUMMARY OF THE INVENTION

The three-dimensional spine remedying apparatus of the invention comprises the following devices: a frame for mounting mechanisms and driving devices of said apparatus; a cephalothoracic board, which is fixed on said frame, for supporting and securing the upper torso of the patient, and capable of moving horizontally along the longitudinal axle (X) of said apparatus; and a device for driving said cephalothoracic board; a hip-leg board, which is fixed on said frame, for supporting and securing the lower torso of the patient, and capable of rotating around the lateral axle (Y) and the longitudinal axle (X) of said apparatus; a device for rotating said hip-leg board around the axle Y; and a device for rotating said hip-leg board around the axle X; and an electric control system for controlling the moving speed and distance of foregoing mechanisms, wherein said apparatus further includes a hip board fixed on said hip-leg board, which is capable of rotating around the vertical axle (Z) of said apparatus; and a device for driving said hip board.

According to one aspect of the invention, said device for driving the cephalothoracic board is a high-speed magnetic driving device using the magnetic force between an electromagnet and a permanent magnet (or electromagnet).

According to another aspect of the invention, said cephalothoracic board further includes a low-speed draught device fixed on said frame, which is used to link up the movement of said high-speed magnetic driving device and the low-speed draught device.

According to another aspect of the invention, said device for rotating said hip-leg board around the longitudinal axle (X) and said device for rotating said hip board around the vertical axle (Z) are both driven by a pair of electromagnets. When electric current passes through one of a pair of electromagnets, said hip-leg board or hip board is driven to rotate in a certain direction by a predetermined angle. When impulse current is alternately transmitted to the paired-electromagnets, said hip-leg board or hip board would make angular oscillation continuously in opposite directions (positive and negative). The frequency of said angular oscillation could be controlled within the range of 20 times/sec by changing the frequency of said impulse current.

According to still another aspect of the invention, mechanisms for precisely limiting the moving distance or the rotation angle are provided in each device for driving said cephalothoracic board, hip-leg board, or hip board.

In addition, the means for securing the body of the patient and the tightness of said securing means are also provided in said cephalothoracic board, hip-leg board, and hip board of the invention.

DESCRIPTION OF A PREFERRED EMBODIMENT OF THE INVENTION

The preferred embodiment of the present invention will be described with reference to the drawings. It should be understood that the embodiment is only to illustrate the invention, not to limit its scope. The scope of protection of the invention should be defined by the appended claims.

Figure 1:
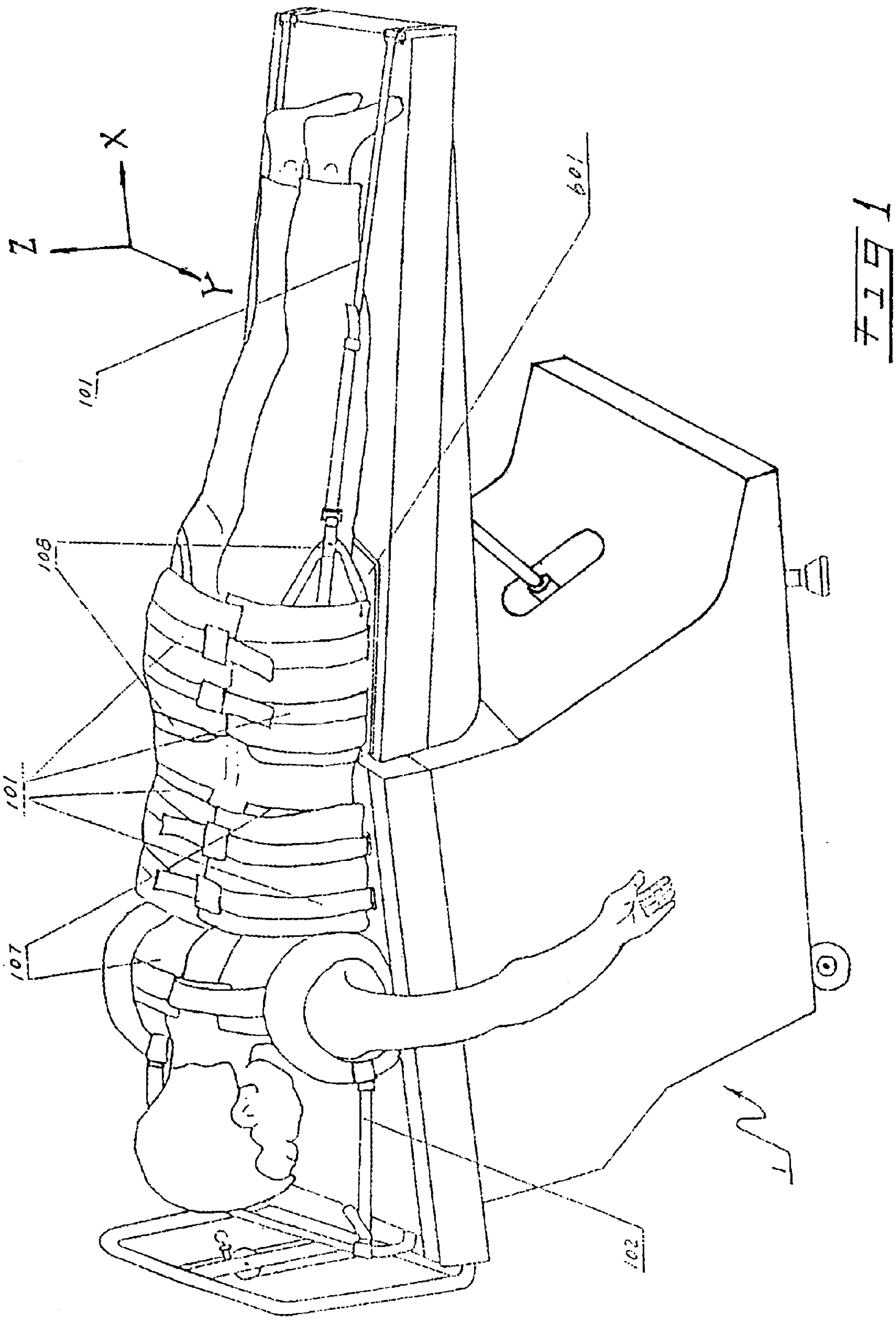
FIG. 1 is an exterior perspective view of the three-dimensional spine remedying apparatus of the present invention.

FIG. 1 is a perspective view of an embodiment of the three-dimensional spine remedying apparatus of the present invention. In FIG. 1, reference number 1 denotes the case-shaped frame on which all the components of the apparatus are mounted. The electric control device (not shown) of the apparatus may be arranged on either side of the frame. As shown in FIG. 1, the patient lying face down on the apparatus is being treated.

Figure 2:
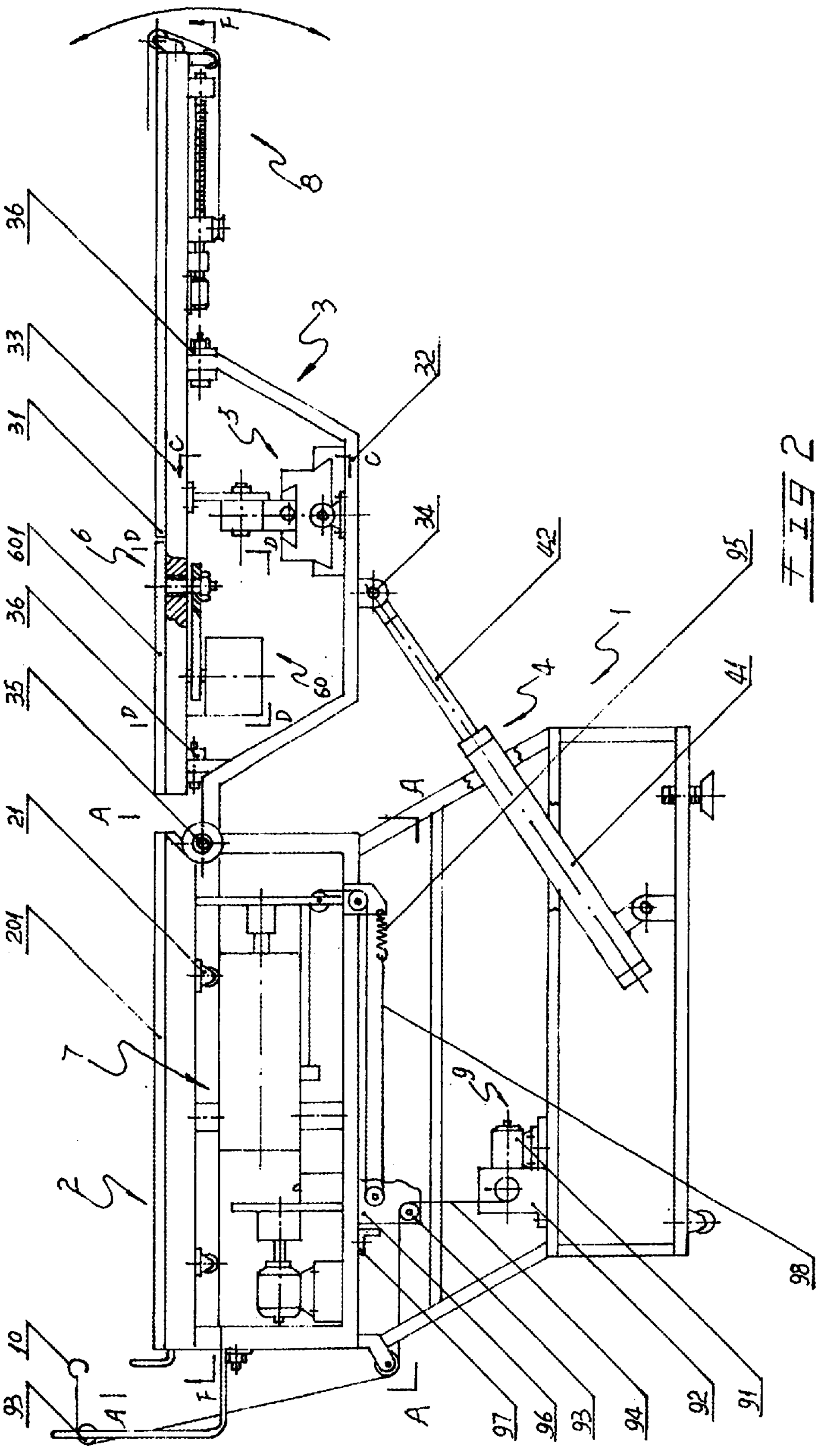
FIG. 2 is a side view of the three-dimensional spine remedying apparatus of the present invention.

Now referring to FIG. 2, the cephalothoracic board device 2 is arranged on the frame 1, wherein the cephalothoracic board 201 is supported by four wheels 21, which move along the rails on the frame 1. The magnetic driving device 7 for moving the cephalothoracic board device 2 horizontally along the axle X is positioned centrally above the frame 1, below the device 2.

The hip-leg board device 3 is composed of a hip-leg board 31, a bow shaped shelf 32 and a long frame 33. The hip-leg board 31 is fixed on the long frame 33. The long frame 33 which is connected with the shelf 32 by two hinge axes 36 can rotate around the axle X. The shelf 32 is able to rotate around the axle Y with its left end mounted on the frame 1 by the hinge axle 35. The lower portion of the shelf is supported on the driving device 4 by a pintle 34. Said driving device 4 consists of a swaying hydraulic cylinder or an air cylinder 41. When the plunger 42 is extending or retracting, the shelf 32, i.e. the entire hip-leg board device 3 is driven to rotate around the axle Y by a certain angle.

The reference number 5 denotes the driving device 5, which is mounted inside the bow shaped shelf, for rotating said long frame 33 and said hip-leg board 31 around the axle X. The reference number 6 denotes the hip board device which is mounted on the long frame 33 with a hip board 601 on the top, the upper face of the hip board is flush with that of the hip-leg board 31. The hip board 601 mounted on the long frame 33 can rotate around the axle Z, and is driven by the hip board's driving device 60. The description and the working process of the hip-leg board device 3 and the hip board device 6 as well as the driving devices thereof are to be followed.

The reference number 8 in FIG. 2 denotes the device for adjusting the degree of tightness of the securing device for securing the body of the patient, which will be described in detail.

The reference number 9 denotes the low-speed draught device, and the reference number 10 denotes the hook for draughting. In the draught device 9, a motor 91 drives the winding drum in the rolling device 92 to rotate and, subsequently, the hauling rope 94 is dragged through a pulley 93. As a result, the hook 10 fixed on the free end of the hauling rope 94 is able to draught the headgear (not shown in the figure) which is attached to the head of the patient, i.e. draught the vertebra cervicalis at a low speed. In addition, the bracket 96 for installing the first pulley 93 can move along the axle X on the slide rail of the frame 1 (not shown in the figure). However, the further leftward movement of the bracket 96 is stopped by the limit stop 97 mounted on the frame 1.

Now, the structures of the driving device of the cephalothoracic board device 7 and the high-low speed linking up clutch for linking up the movement between the low-speed draught device and said driving device are to be described with reference to FIG. 3.

Figure 3:
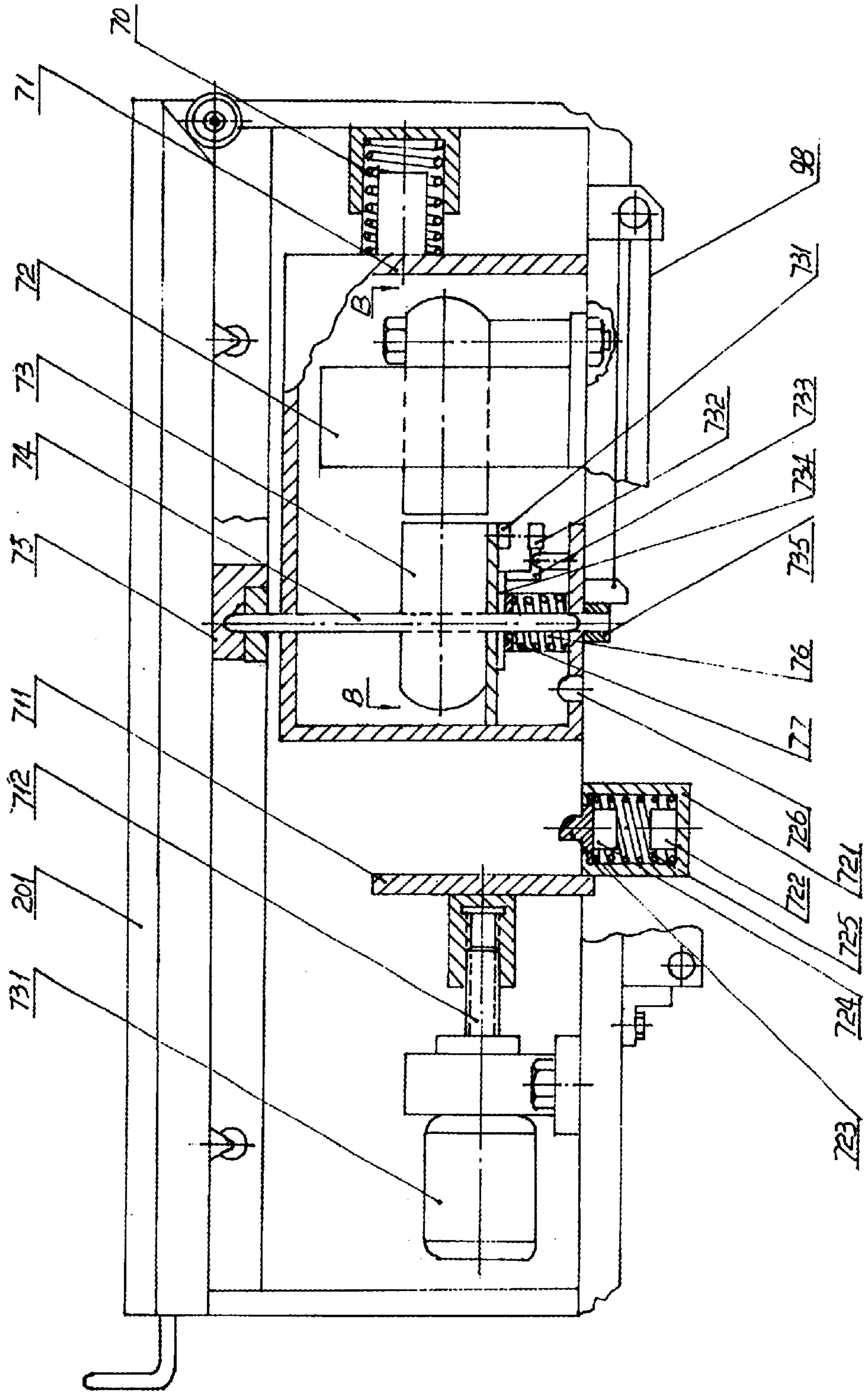
FIG. 3 is an enlarged view illustrating the structures of the device for driving the cephalothoracic board in accordance with the present invention and the high-low speed linking-up clutch, which is used to link up the movement of said driving device with the movement of the low-speed draught device.
Figure 4:
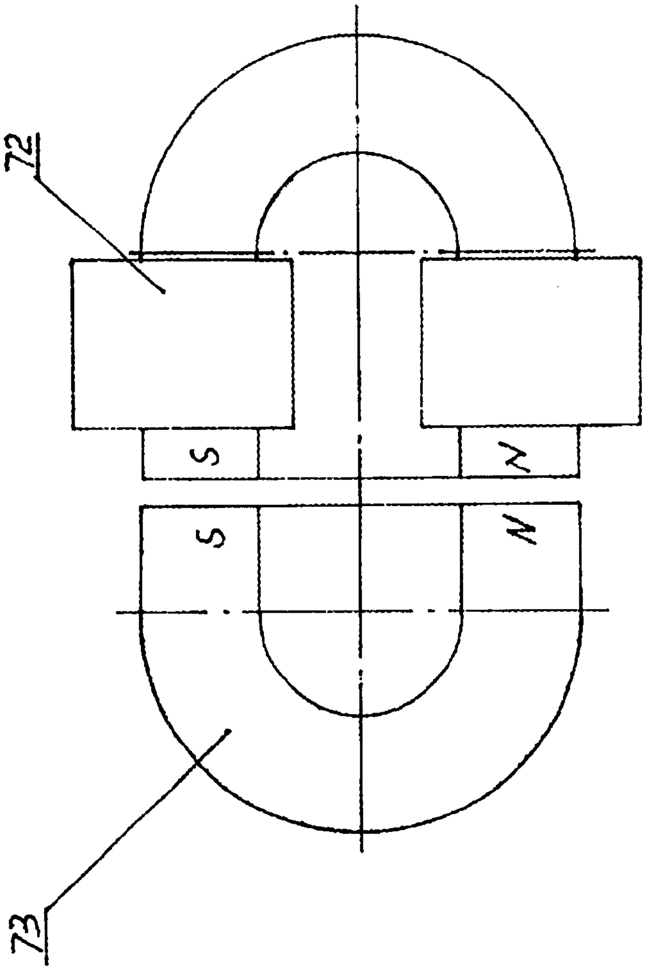
FIG. 4 is a view taken along lines IV—IV in FIG. 3, illustrating the magnetic polarity.

The reference number 71 in FIG. 3 is a box shaped case, the dextral bottom of which is open. Some wheels which can move along the axle X on the slide rails of the frame 1 are provided on both sides of the case 71. The immovable electromagnet 72 positioned on the right-hand side of the case 71 is fixed on the frame 1 by a bolt, while the movable permanent magnet 73 which can move relative to the immovable electromagnet 72 is fixed on the left-hand side of the case 71. The reference number 70 denotes a compression spring. When the electromagnet 72 is not electrified, the permanent magnet 73 moves rightward to the electromagnet 72 due to the magnet attraction therebetween, and thus compressing the spring 70. When the electromagnet 72 is electrified, the polarities of the two magnets shown in FIG. 4 are repelling each other. As a result, the permanent magnet 73 fixed in the case 71 moves leftward along with the case. Since the electromagnetic force is generated rapidly and the force of the spring 70 and the electromagnetic force are in the same direction, the case 71 moves leftward at an accelerated speed. Alternatively, said permanent magnet 73 can be replaced with an electromagnet on condition that the same polarities of the two electromagnets are face to face as the repelling effect of the two electromagnets is required.

The reference number 74 in FIG. 3 denotes a pin which passes through the permanent magnet 73 into the case 71 and can slide along the axle Z within the case 71. When the cephalothoracic board device 2 is required to move leftward quickly, the spring 76 at the bottom of the case 71 jacks up the flange 77 at the lower end of the pin 74, making the upper end of the pin 74 inserted into the hole on the limit stop 75, which is fixed on the cephalothoracic board 201. And then, the body of the patient is rapidly draught leftward along the axle X by the cephalothoracic board device, so as to treat diseases such as prolapse of lumbar intervertebral disc.

The reference number 711 in FIG. 3 denotes a baffle which is oriented by the guide rail on the frame 1 and used to limit the distance of the leftward movement of the case 71, i.e. of the cephalothoracic board device 2. A screw 712, which is screwed into the bolt hole in the rear of the baffle 711, is driven by the motor 713, so as to adjust the movement distance of the baffle 711, i.e. of the cephalothoracic board device 2. In this way, a precise hauling distance is ensured without injuring the patient.

In order to prevent the case 71 from rebounding after it knocks against the baffle 711, an arresting device including a case 721 fixed on the lower portion of the baffle 711 is provided. Said case 721 includes a small electromagnet 722 mounted on its bottom, a ferromagnet 724 below the stopper 723, a compression spring 725 positioned between the ferromagnet 724 and the electromagnet 722, wherein the spring 725 is used to push up the stopper 723. Both the upper right edge of the stopper 723 facing the case 71 and the lower left edge of the case 71 are chamfered to a round corner. When the case 71 moves toward the baffle 711, its lower edge contacts with the upper edge of the stopper 723, and the stopper 723 is forced to move down by means of the round corners on both sides against the spring 725. When the case 71 passes the stopper 723, the stopper 723 is pushed up by the spring 725 and enters into the recess 726 on the case 71 to limit the movement of the case 71. In this way, the rebounding of the case 71, i.e. of the driving device 7 of the cephalothoracic board, is prevented. When the case 71 is required to move back, the electromagnet 722 is electrified so that the stopper 723 is forced down and exits the recess 726, hence the case 71 is reset automatically via the magnetic force of the permanent magnet.

The structure and the working process of the high-low speed linking-up clutch for linking up the movement of said high-speed magnetic driving device with that of said low-speed draught device 9 will be described hereinafter.

The working process of the low-speed draught device 9 has already been described above. Said clutch is needed when the hook 10 is required to speed up suddenly in the draughting process. Said clutch is composed of an electromagnet 731 fixed in the case 71 and a lever 733 which is pivotally connected with a column fixed on the bottom of the case 71. A ferromagnet 732 is fixed on the right end of the lever 733 and a fork 734 is fixed on the left end. The notch in the middle of the fork 734 is clamped on the sides of the pin 74 , with the lower face of the fork 734 pressing against the upper face of the flange 77 on the lower portion of the pin 74. In addition, a slide block 735 which can move on the slide rail of the frame along the axle X is placed below the case 71. A pinhole for accommodating the pin 74 is provided on the slide block 735. Under the non-operating state, the hauling rope 98 draughts the slide block 735 to the right by means of a tension spring 95, forcing said slide block 735 to lean against a distance piece. In this state, the pin 74 is aligned exactly with the hole on the slide block 735. If the electromagnet 731 is electrified at this time, it will attract the ferromagnet 732 upwards, causing the lever 733 to rotate around its pivot. So, the flange 77 of the pin 74 is pushed down by the fork 734 at the left end of the lever, and the lower end of the pin 74 is forced into the hole of the slide block 735 when the elastic force of the spring 74 is overcome.

When the draught force of the low-speed draught device reaches a predetermined value, the immovable electromagnet 72 is electrified, and then the high-speed driving device of said cephalothoracic board begins to work, so that the permanent magnet 73 moves to the left rapidly. However, the slide block 735 is being driven this time instead of the cephalothoracic board device 2. As a result, the slide block 735 drives the slide plate 96 rapidly to the right by using a pulley (refer to FIG. 2) and a hauling rope around the pulley, so that the hook 10 which is moving slowly suddenly speeds up. This is especially suitable for treating cervical spondylopathy.

Now, the structures and working processes of the hip-leg board device as well as the device for rotating said hip-leg board device around the axle X will be described with reference to FIG. 5.

Figure 5:
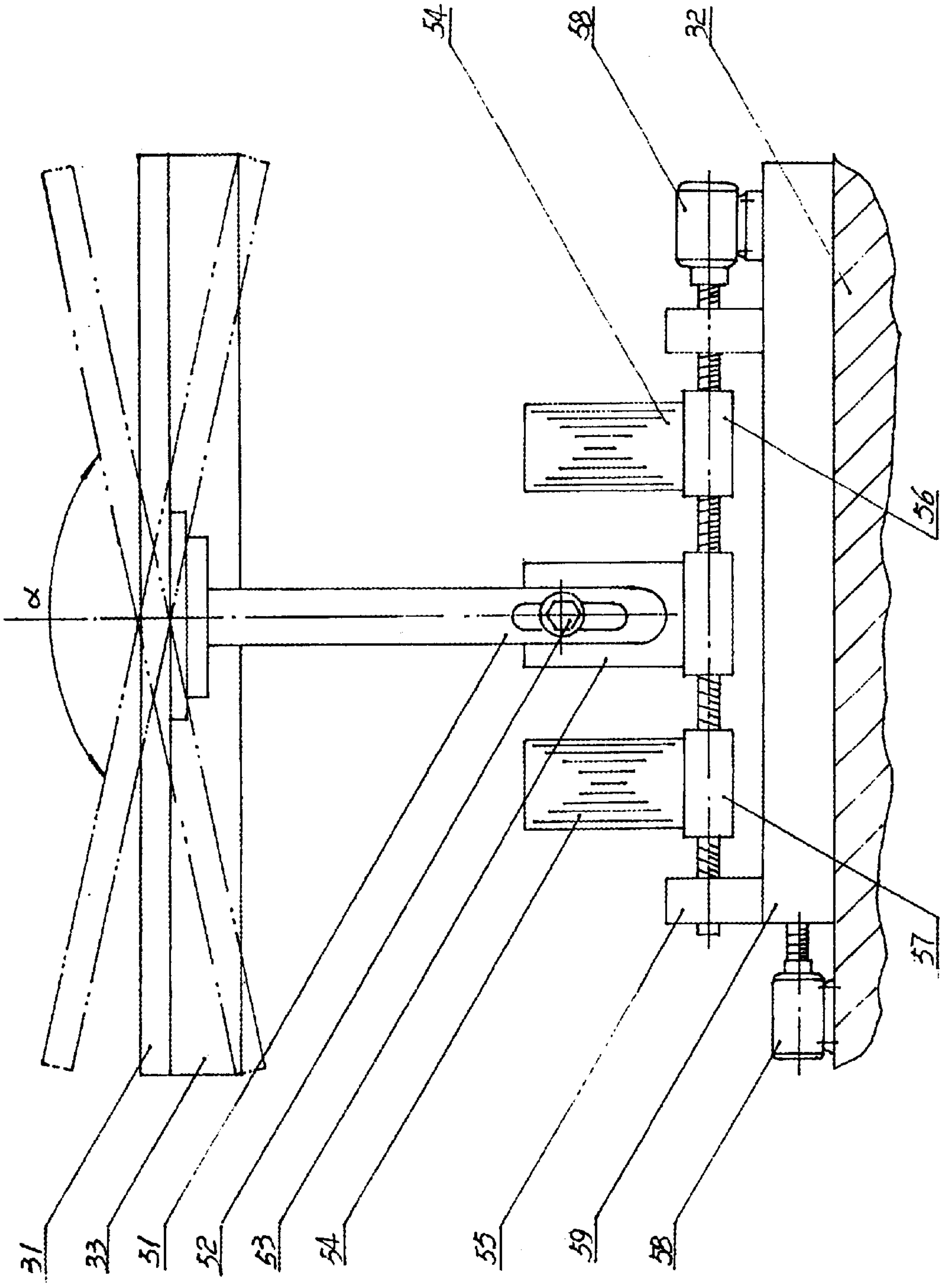
FIG. 5 is a schematic diagram illustrating the structure of the device for rotating the hip-leg board around the axle X and the working condition of the hip-leg board.

In FIG. 5, an oscillating lever 51 is mounted below the hip-leg board 31 which is fixed on the long frame 33. At the lower end of the oscillating lever 51 is a long slot in which a pin 52 is inserted and capable of freely sliding up and down. The reference number 53 denotes a ferromagnet moving along the axle Y, in which said pin 52 is mounted. When the ferromagnet 53 moves left and right along the axle Y, the hip-leg board 31 and the long frame 33 supported by the hinge axle 36 rotate around the axle X due to the relative slide between the pin 52 and the long slot at the lower end of the oscillating lever 51.

Said ferromagnet 53 is driven by two electromagnets 54 arranged at both sides of it. Two nuts 56, 57 are separately fixed at the lower end of each electromagnet 54 and connected with a lead screw 55, wherein the helical directions of the nuts 56 and 57 are opposite, and so are those of the threads at the two ends of the lead screw 55. Said lead screw 55 is mounted on the abutments of the slide plate 59 and driven by the motor 58 on the rightside. By starting the motor 58 to rotate the lead screw 55, the space between the two electromagnets 54 and the ferromagnet 53, i.e. the sway angle a of the hip-leg board 31, is adjusted. In addition, the slide plate 59 can be driven by the lead screw which is turned by another motor 58 on the left side, so that the slide plate 59 can slide along the axle Y. When the slide plate 59 moves to the right, the left electromagnet 54 comes closer to the ferromagnet 53, whereas the right electromagnet 54 departs from the ferromagnet 53, and vice versa. At this time, the sway angle a of the hip-leg board 31 remains unchanged, but the angle of its sway between the two sides is different.

If one of the electromagnets 54 is electrified, the ferromagnet 53 will be attracted, and the hip-leg board 31 will sway toward one side and then stay on that position. If both electromagnets 54 are electrified with impulse current alternately, the hip-leg board 31 will sway from side to side successively (angular oscillation), wherein the frequency of the oscillation depends on the frequency of the impulse current.

The swaying of the hip-leg board 31 in a certain direction is able to correct the angular displacement between the vertebras, whereas the continuous swaying between the two directions (angular oscillation) is able to relax the muscles, and further to treat diseases such as the strain of lumbar muscles.

Now, according to FIGS. 6 and 7, the structures and working process of the hip board device 6 and the device 60 for rotating the hip board device 6 around the axle Z will be described. It should be noted that FIG. 6 is an upward view.

Figure 6:
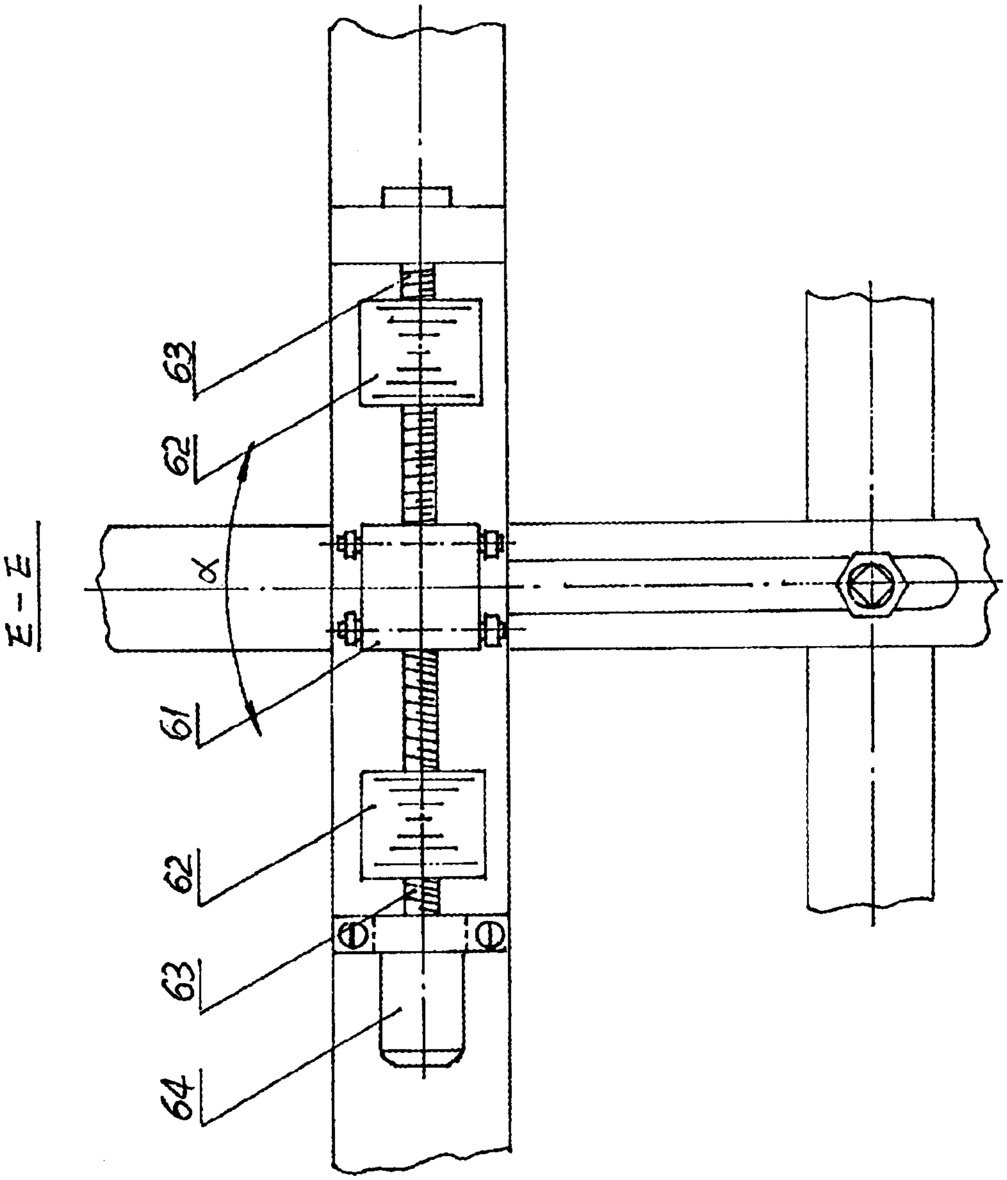
FIG. 6 is a sectional view of the direction of the arrow U in FIG. 2, illustrating the structure of the device for rotating the hip board around the axle Z.

The reference number 61 in FIG. 6 denotes a ferromagnet, on both side s of which two electromagnets 62 are arranged separately. Similar to the structure and the working principle of the magnetic mechanism in said driving device 5, two nuts having opposite helical directions are separately fixed on two electromagnets 62 and driven by a lead screw 63 which is turned by a motor 64, so as to adjust the distance between the ferromagnet 61 and the two electromagnets 62 simultaneously. In addition, the entire driving device 60 is mounted on the long frame 33 of the hip-leg board device 3.

Figure 7:
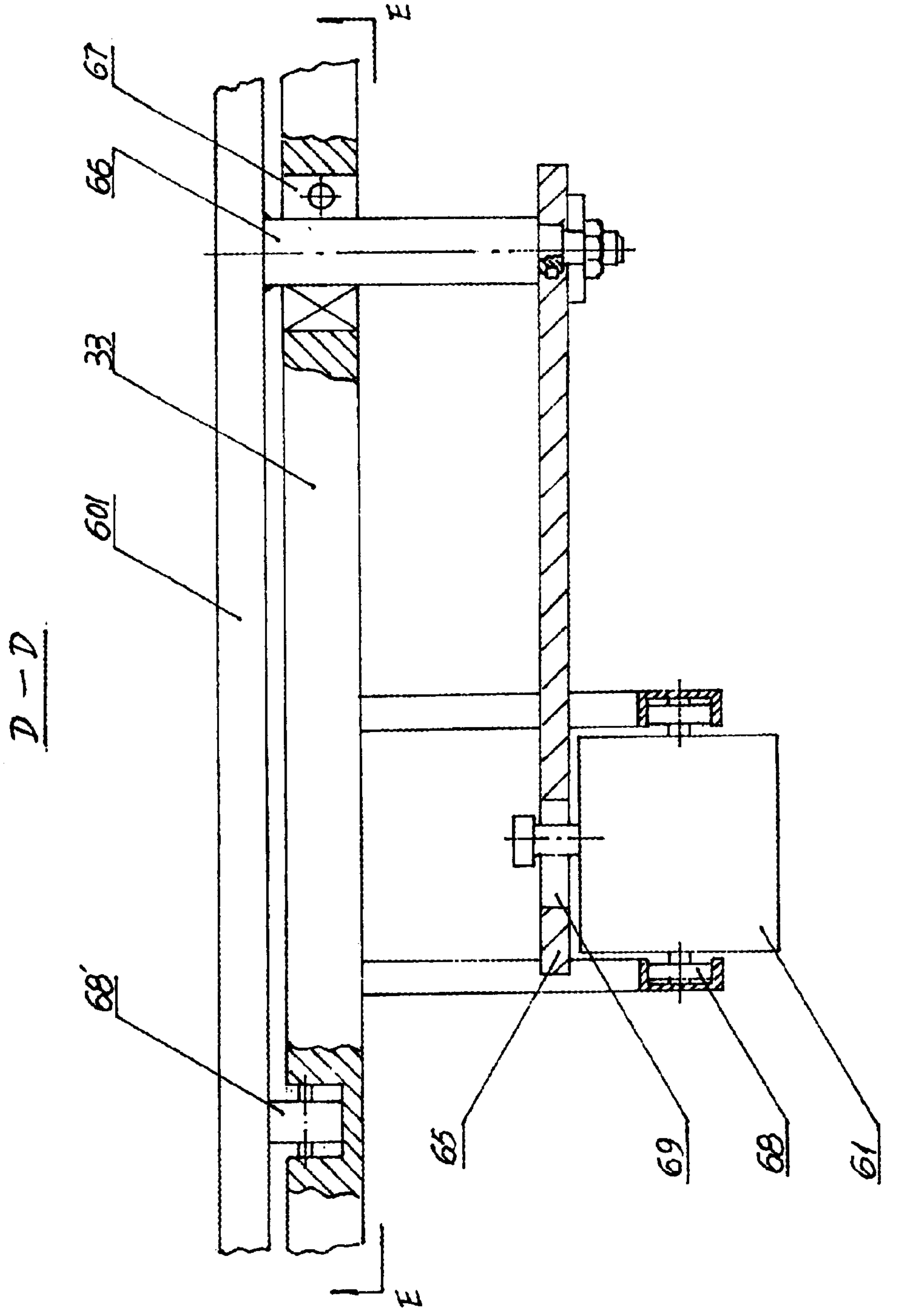
FIG. 7 is a cross-sectional view taken along lines VII—VII in FIG. 6.

Referring to FIG. 7, the reference number 65 denotes a swing rod, one end of which is fixed on an axle 66 by using a key or other means. And said axle 66 is welded on the lower surface of the hip board 601, and is supported by a bearing 67 installed in the long frame 33. The lower surface of the hip board 601 is a slightly higher than the upper surface of the long frame 33, and the hip board 601 is supported by several trolleys 681 or roller bearings mounted in the long frame 33. A long slot 69 is notched at the other end of the swing rod 65, and a pin fixed on the ferromagnet 61 extends upward into the long slot 69, in which the pin can move in relation to the swing rod 65. In addition, the ferromagnet 61 is provided with trolleys 68 on both sides which are supported by the rails on the long frame 33 and can roll on said rails.

Similar to the driving device 5, if only the electromagnet 62 at one side of the ferromagnet 61 is electrified, the ferromagnet 61 will be attracted by the electromagnet to shift toward it. At this time, the swing rod 65 is driven by the pin on top of the electromagnet 61 which is inserted into the long slot 69, and accordingly drives the axle 66, i.e. the hip board 601, to rotate around the axle Z, when the electromagnets 62 at both sides of the ferromagnet 61 are electrified with impulse current alternately, the ferromagnet 61 drives the swing rod 65, the axle 66 and the hip board 601 to sway left and right (angular oscillation), wherein the frequency of the oscillation depends on the frequency of the impulse current.

Also, the rotation of the hip board 601 in one direction is used to remedy the angular replacement between vertebras, whereas the continuous vibration (angular oscillation) of the same is used to relax the muscles, and further to treat diseases such as the strain of lumbar muscles.

Figure 8:
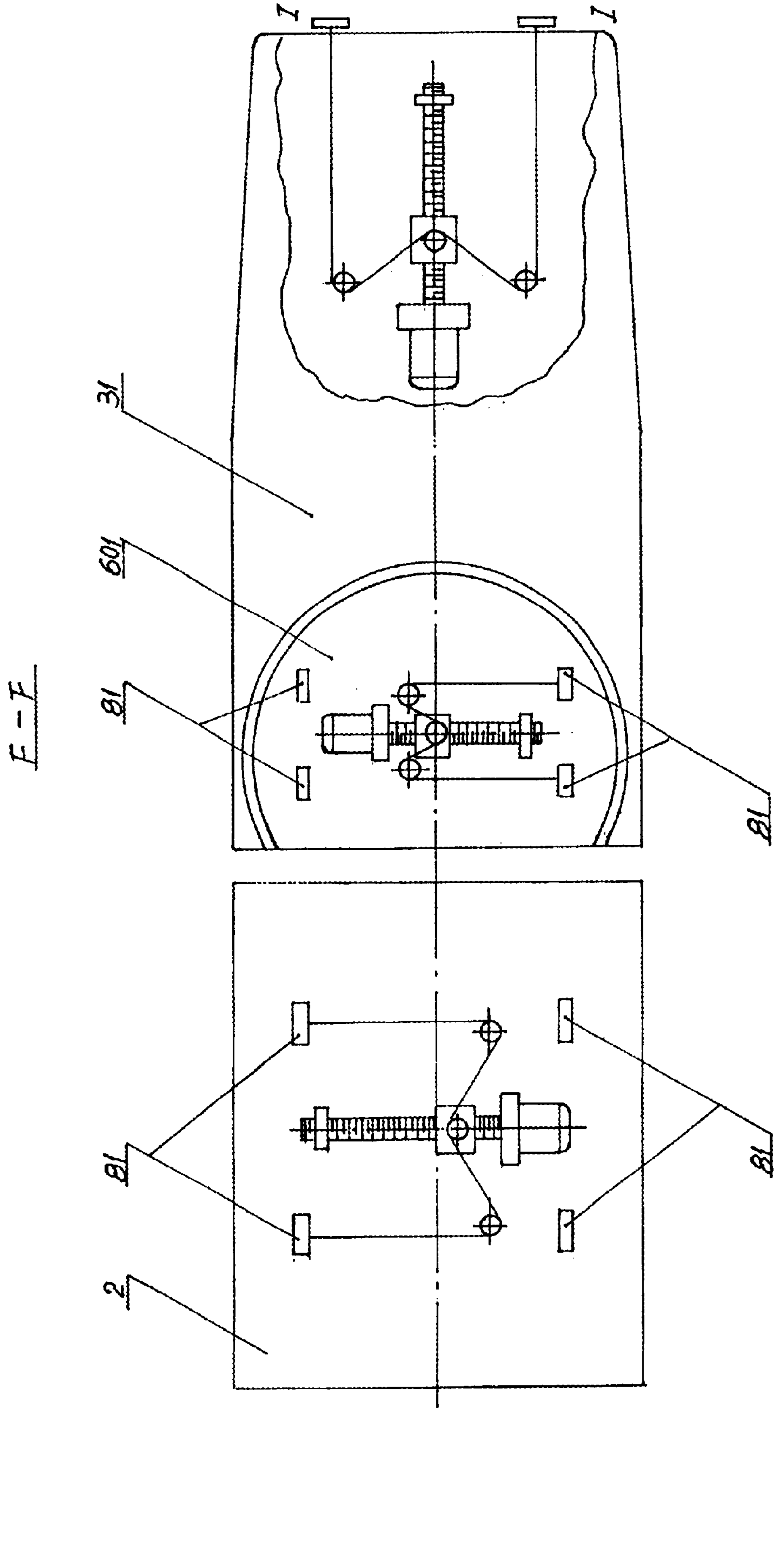
FIG. 8 is a layout schematic diagram showing the hole for accommodating the securing belt used to secure the torso of the patient and the device for adjusting the degree of tightness of the securing belt.

FIG. 8 illustrates the adjusting devices 8 which are mounted on the back of said plates 2, 31 and 6 for adjusting the degree of the tightness of the securing belts and the positions of the slot holes 81 by which the securing belts pass through the cephalothoracic board 2 and hip board 601.

Figure 9:
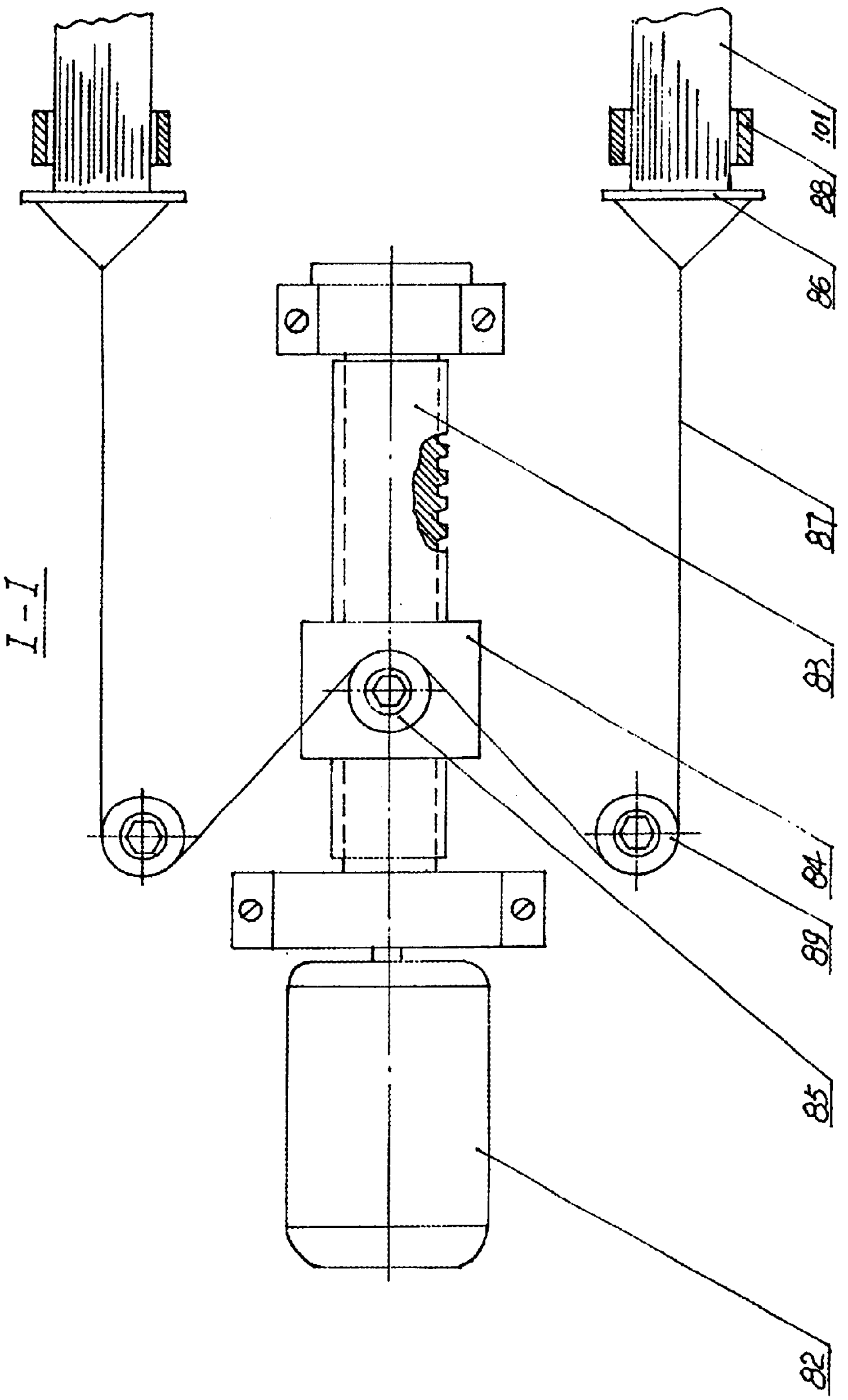
FIG. 9 is a schematic diagram showing the device for adjusting the degree of tightness of the securing belt used to secure the torso of the patient.

FIG. 9 is a structure chart of the adjusting device 8. A lead screw 83 is mounted on the driving axle of the motor 82 and a nut 84 is mounted on said lead screw 83. In addition, a rope pulley 85 is mounted on the nut 84 and it can move along with the nut. A taut wire 87 passes by the rope pulley 85 and two immovable rope pulleys 89. The two free ends of the wire 87 are fastened to one side of two connecting plates 86 and the securing belts 101 are connected with the other side of the connecting plates. The other end of the securing belts 101 connected with the securing belt on the other side shown in FIG. 1 or other taut pieces after passing through the gap of the Π shaped plates 88 and the slot holes 81 shown in FIG. 8.

The lead screw 83 begins to rotate when the motor 82 is started and drive the nut 84 together with the rope pulley 85 mounted thereon to move leftward. And then the two ends of the taut wire 87, which are connected with the connecting plates 86, move rightward, so that the securing belts 101 are fastened enough to secure the torso of the patient. When the motor 82 rotates in the reverse direction and drives the nut 84 and the rope pulley 85 to move rightward, the securing belts will be loosened. However, since the width of the connecting plate 86 is larger than that of the gap in the middle of the Π shaped plate 88, the securing belt 101 is able to loosen to such an extent as permitted by the Π shaped plate 88.

Figure 10:
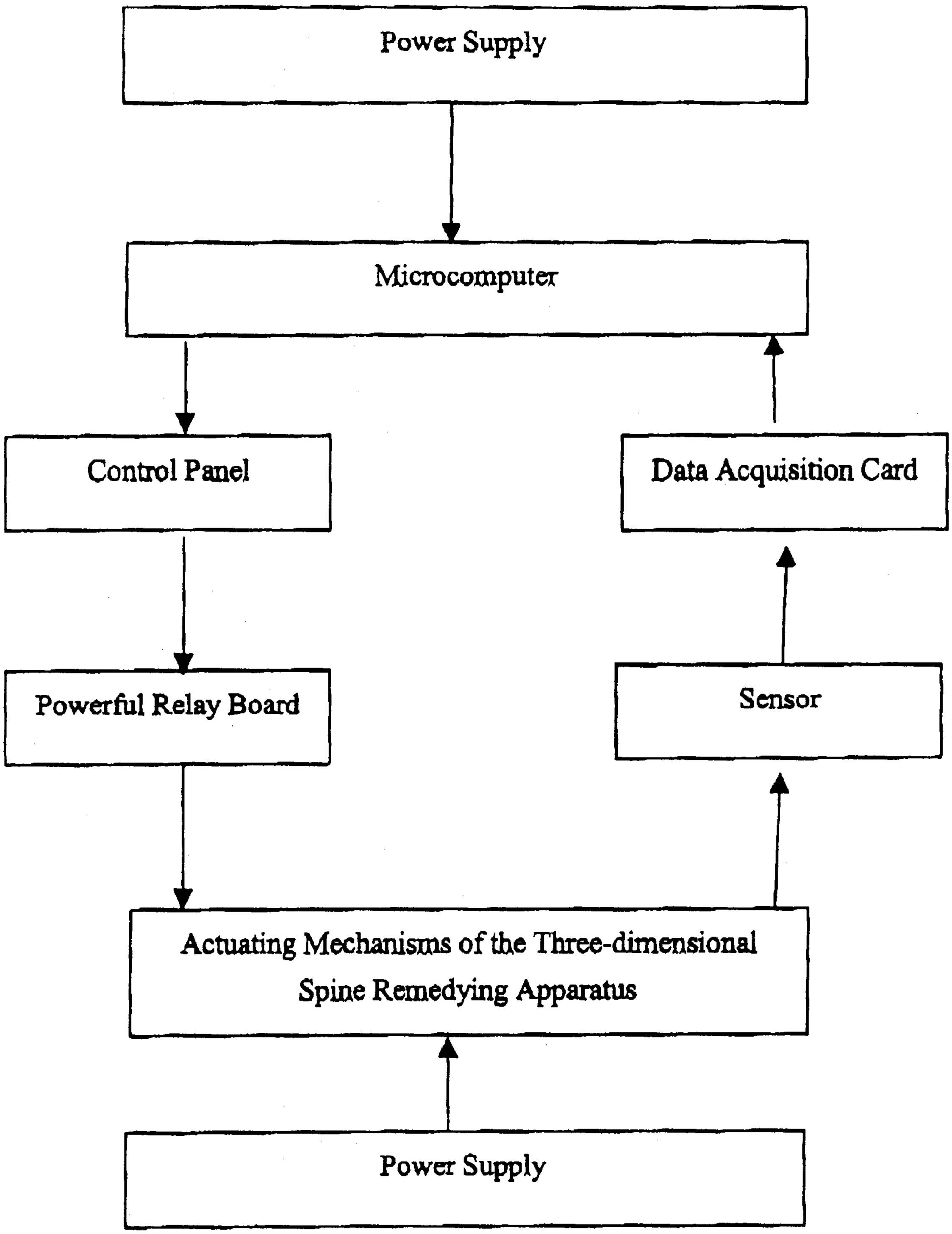
FIG. 10 is a block diagram showing the electric control system of the three-dimensional spine remedying apparatus in accordance with the present invention.

FIG. 10 is a block diagram showing the electric control system, under which all the working mechanisms of the present apparatus can be controlled by a microcomputer, which is advantageous to the course of treatment.

Industrial Application

The apparatus of the present invention is an improvement on the prior art considering that the pathological change between vertebras is often three-dimensional, with the linear displacement and the angular displacement occuring synchronously. Moreover, according to the principle of the physiology, the faster the speed of the stimulation to the muscles and the nerves within the range of safety, the lighter the degree of suffering. Known from the medical practice, the faster the speed of the draught (linear displacement) and the angular displacement, the higher the instantaneous negative pressure between the vertebras, and the higher the pressure between the rear ligament and the intervertebral disc, which is in favor of reposition or replacement, and the relieving of the conglutination between the nerve roots and the surrounding tissues. Therefore, the apparatus of the present invention has excellent curative effect for parenchyma trauma between vertebras such as prolapse of lumbar intervertebral disc and cervical spondylopathy. In addition, the apparatus can also be used to treat strain of lumbar muscles.

Compared with the prior art, the apparatus of the invention includes the following advantages:

1. Since the apparatus of the present invention can not only draught along the axle X, but also have the hip-leg board and the hip board rotate around the three axle (X, Y, Z). Therefore, it may be used to treat pathological changes in various positions, which would improve the curative effects.

2. Since an electromagnetic driving device is adopted in the apparatus of the invention, the draught speed is much faster than hydraulically or mechanically driven device, wherein the time of the draught process can be less than 0.1 second. As a result, the patient would not be uncomfortable or frightened in the treatment process, and thus the curative effects would be improved.

3. Since devices for presetting distance are provided in all high-speed driving devices, the draught distance and the angle of swing are limited in the range of safety and efficiency. Therefore the extension of the parenchyma attached to vertebras, such as ligaments or muscles, would not exceed the limitation (usually is 4–7 mm), so that the parenchyma would not be injured. So the apparatus of the invention is absolutely safe to the patient.

4. A high-speed driving mechanism and a low-speed driving mechanism are provided in the linear draught driving device of the cephalothoracic board device. Furthermore, the motions of said two mechanisms are linked up by a clutch device. In addition, the hip-leg board and the hip board can be driven to make a rapid vibration by the driving devices thereof, wherein the vibration can relax the muscles. Therefore, the apparatus of the invention can imitate the massage for bonesetting in traditional Chinese medical science and replace the manual massage. In addition, the velocity, distance and angle of the motions in all the mechanisms are adjustable and can be controlled by computer, so that the problem of how to determine the strength and magnitude of the massage in Chinese traditional medicine is properly solved.

5. Since a device for securing the body of the patient is provided, and the tightness and adjusting of the securing belt can be controlled by mechanism and computer, and the strength of the securing is limited within a suitable range.

6. The noise of the electromagnetic driving is low and transient, which is suitable for treatment.

What is claimed is:

1. A three-dimensional spine remedying apparatus comprising:

a frame;

a cephalothoracic board mounted on said frame for supporting and securing an upper torso of a patient, said cephalothoracic board being movable horizontally along a longitudinal axle (X) of the apparatus;

a first drive for driving said cephalothoracic board;

a long board mounted on said frame for supporting a lower torso of the patient, said long board being rotatable around a lateral axle (Y) and the longitudinal axle (X) of said apparatus;

a hip-leg board mounted on said long board;

a second drive for rotating said hip-leg board around the lateral axle (Y);

a third drive for rotating said hip-leg board around the longitudinal axle (X);

an electric control system for controlling a speed and a distance of the motions of each of the first, second and third drives;

a hip board mounted on said long board and rotatable around an axle (Z) of said apparatus that is vertical when said long board is at least substantially horizontal; and a fourth drive for driving the hip board.

2. The apparatus according to claim 1, further comprising:

a low-speed traction device mounted on said frame;

a high-speed driving device of said cephalothoracic board; and a clutch for selectively connecting the low-speed traction device and the high speed driving device with the cephalothoracic board.

3. The apparatus according to claim 1, wherein the apparatus further comprises a mechanism for precisely limiting the distance or the rotation angle in each drive of each of said cephalothoracic board, said hip-leg board and said hip board.

4. The apparatus according to claim 3, wherein securing means for securing a body of the patient and adjusting a degree of tightness are provided in said cephalothoracic board, hip-leg board and hip board.

5. The apparatus according to claim 1, wherein said first drive is a high-speed magnetic driving device utilizing a magnetic force between an electromagnet and a permanent magnet or an electromagnet.

6. The apparatus according to claim 1, wherein the third and fourth drive are both driven by a magnetic driving mechanism using a pair of magnets.

7. The apparatus according to claim 6, wherein when an electric current passes through a magnet of the paired magnets, said hip-leg board or hip board are driven to rotate by a predetermined angle, whereas when an impulse current is alternately transmitted to the paired magnets, said hip-leg board or hip board will continuously vibrate in two opposite directions (angular oscillation).

8. The apparatus according to claim 1, wherein the axle (Z) is normal to a plane of said long board.

* * * * *

UNITED STATES PATENT AND TRADEMARK OFFICE

CERTIFICATE OF CORRECTION

PATENT NO. : 6,328,759 B1
DATED : December 11, 2001
INVENTOR(S) : Jilin Zhang

It is certified that error appears in the above-identified patent and that said Letters Patent is hereby corrected as shown below:

Title page,
Item [76], Inventor, change "Ji Ling Zhang" to -- Jilin Zhang --

Signed and Sealed this

Thirteenth Day of August, 2002

*Attest:*

JAMES E. ROGAN

*Attesting Officer*

*Director of the United States Patent and Trademark Office*